US011564737B2

(12) United States Patent
Lindquist et al.

(10) Patent No.: US 11,564,737 B2
(45) Date of Patent: *Jan. 31, 2023

(54) MEDICAL DEVICE BALLOON

(71) Applicant: Boston Scientific Scimed, Inc., Maple Grove, MN (US)

(72) Inventors: Jeffrey S. Lindquist, Maple Grove, MN (US); Cass A. Hanson, St. Paul, MN (US); Patrick A. Haverkost, Corcoran, MN (US); Daniel J. Horn, Shoreview, MN (US); Martin R. Willard, Burnsville, MN (US); Derek C. Sutermeister, Ham Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1237 days.

This patent is subject to a terminal disclaimer.

(21) Appl. No.: 15/942,863

(22) Filed: Apr. 2, 2018

(65) Prior Publication Data

US 2018/0221086 A1  Aug. 9, 2018

Related U.S. Application Data

(63) Continuation of application No. 14/513,101, filed on Oct. 13, 2014, now Pat. No. 9,962,223.

(Continued)

(51) Int. Cl.
*A61B 18/12* (2006.01)
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/0022* (2013.01);
(Continued)

(58) Field of Classification Search
CPC .... A61B 2018/0016; A61B 2018/1467; A61B 2562/164; A61B 2562/166; A61B 2018/00214; A61B 2018/0022–00261
See application file for complete search history.

(56) References Cited

U.S. PATENT DOCUMENTS

| 3,427,715 A | * | 2/1969 | Mika | H05K 1/0278 |
| | | | | 439/55 |
| 6,927,344 B1 | * | 8/2005 | Gall | H05K 1/0278 |
| | | | | 174/254 |

(Continued)

FOREIGN PATENT DOCUMENTS

WO    2015027096 A1    2/2015

OTHER PUBLICATIONS

Communication pursuant to Article 93(3) EPC for application No. EP14789482.8, dated Mar. 13, 2019, 9 pages.

*Primary Examiner* — Jaymi E Della
(74) *Attorney, Agent, or Firm* — Seager, Tufte & Wickhem, LLP

(57) ABSTRACT

Medical devices and methods for making and using medical devices are disclosed. An example medical device may include a catheter shaft. An expandable member may be coupled to the catheter shaft. The expandable member may be capable of shifting between a folded configuration and an expanded configuration. A plurality of flexible elements may be attached to the expandable member, with a plurality of electrode assemblies disposed on the flexible elements. The flexible elements may have a grooved substrate.

19 Claims, 14 Drawing Sheets

Related U.S. Application Data

(60) Provisional application No. 61/891,257, filed on Oct. 15, 2013.

(52) U.S. Cl.
CPC ............... *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/00797* (2013.01); *A61B 2018/00815* (2013.01); *A61B 2018/1465* (2013.01); *A61B 2018/1467* (2013.01); *A61B 2018/1475* (2013.01); *A61B 2562/164* (2013.01)

(56) References Cited

U.S. PATENT DOCUMENTS

| | | | | |
|---|---|---|---|---|
| 2004/0054274 A1* | 3/2004 | Finneran | ................ | A61B 5/389 600/546 |
| 2007/0129720 A1* | 6/2007 | Demarais | ........... | A61B 18/1492 606/41 |
| 2008/0188912 A1* | 8/2008 | Stone | ...................... | A61F 7/123 606/192 |
| 2010/0204560 A1* | 8/2010 | Salahieh | .................. | A61B 5/01 606/41 |

\* cited by examiner

MEDICAL DEVICE BALLOON

CROSS-REFERENCE TO RELATED APPLICATIONS

This application is a continuation of U.S. patent application Ser. No. 14/513,101, filed Oct. 13, 2014, now U.S. Pat. No. 9,962,223, which claims the benefit of priority under 35 U.S.C. § 119 to U.S. Provisional Application Ser. No. 61/891,257, filed Oct. 15, 2013, the disclosures of which are incorporated herein by reference in their entirety.

TECHNICAL FIELD

The present disclosure pertains to medical devices, and methods for manufacturing medical devices. More particularly, the present disclosure pertains to medical devices for sympathetic nerve ablation.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a medical device for sympathetic nerve modulation and/or ablation. The medical device may include a catheter shaft, an expandable member coupled to the catheter shaft, the expandable member having a longitudinal axis, a proximal region, a distal region, and a body extending therebetween, and a plurality of flexible elements attached to the body of the expandable member, the flexible elements including a plurality of electrode assemblies, wherein the flexible elements include a substrate having a plurality of elongate grooves formed therein.

Another example medical device may include a catheter shaft, an expandable balloon having a longitudinal axis, a distal waist, proximal waist, and a body extending therebetween, the proximal waist being coupled to the catheter shaft, a flexible substrate attached to the expandable balloon, the substrate including a plurality of grooves formed therein, and a plurality of electrode assemblies disposed on the flexible substrate.

An example method of making a medical device may include forming a plurality of grooves in a substrate, forming an electrical circuit on the grooved substrate, affixing the grooved substrate onto an expandable balloon, and attaching the expandable balloon to a catheter.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
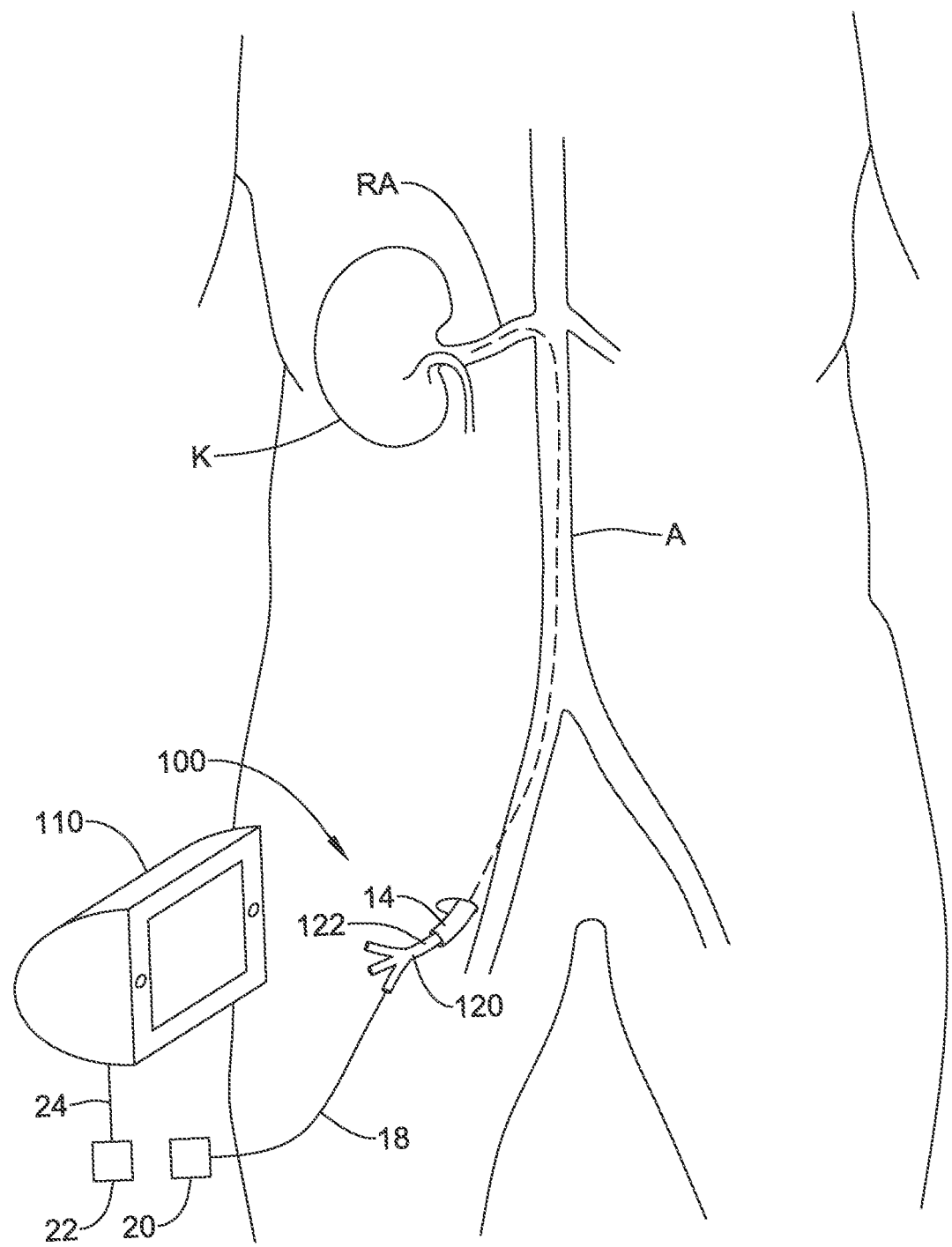
FIG. 1 is a schematic view of an example sympathetic nerve ablation device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

Certain treatments are aimed at the temporary or permanent interruption or modification of select nerve function. In some instances, the nerves are sympathetic nerves. One example treatment is renal nerve ablation, which is sometimes used to treat conditions such as or related to hypertension, congestive heart failure, diabetes, or other conditions impacted by high blood pressure or salt retention. The kidneys produce a sympathetic response, which may increase the undesired retention of water and/or sodium. The result of the sympathetic response, for example, may be an increase in blood pressure. Ablating some of the nerves running to the kidneys (e.g., disposed adjacent to or otherwise along the renal arteries) may reduce or eliminate this sympathetic response, which may provide a corresponding reduction in the associated undesired symptoms (e.g., a reduction in blood pressure).

Some embodiments of the present disclosure relate to a power generating and control apparatus, often for the treatment of targeted tissue in order to achieve a therapeutic effect. In some embodiments, the target tissue is tissue containing or proximate to nerves. In one embodiment, the target tissue includes renal arteries and associated renal nerves. In other embodiments, the target tissue is sympathetic nerves including, for example, sympathetic nerves disposed adjacent to blood vessels. In still other embodiments the target tissue is luminal tissue, which may further comprise diseased tissue such as that found in arterial disease.

In some embodiments of the present disclosure, the ability to deliver energy in a targeted dosage may be used for nerve tissue in order to achieve beneficial biologic responses. For example, chronic pain, urologic dysfunction, hypertension, and a wide variety of other persistent conditions are known to be affected through the operation of nervous tissue. For example, it is known that chronic hypertension that may not be responsive to medication may be improved or eliminated by disabling excessive nerve activity proximate to the renal arteries. It is also known that nervous tissue does not naturally possess regenerative characteristics. Therefore it may be possible to beneficially affect excessive nerve activity by disrupting the conductive pathway of the nervous tissue. When disrupting nerve conductive pathways, it is particularly advantageous to avoid damage to neighboring nerves or organ tissue. The ability to direct and control energy dosage is well-suited to the treatment of nerve tissue. Whether in a heating or ablating energy dosage, the precise control of energy delivery as described and disclosed herein may be directed to the nerve tissue. Moreover, directed application of energy may suffice to target a nerve without the need to be in exact contact, as would be required when using a typical ablation probe. For example, eccentric heating may be applied at a temperature high enough to denature nerve tissue without causing ablation and without requiring the piercing of luminal tissue. However, it may also be desirable to configure the energy delivery surface of the present disclosure to pierce tissue and deliver ablating energy similar to an ablation probe with the exact energy dosage being controlled by a power control and generation apparatus.

In some embodiments, efficacy of the denervation treatment can be assessed by measurement before, during, and/or after the treatment to tailor one or more parameters of the treatment to the particular patient or to identify the need for additional treatments. For instance, a denervation system may include functionality for assessing whether a treatment has caused or is causing a reduction in neural activity in a target or proximate tissue, which may provide feedback for adjusting parameters of the treatment or indicate the necessity for additional treatments.

Many of the devices and methods described herein are discussed relative to renal nerve ablation and/or modulation. However, it is contemplated that the devices and methods may be used in other treatment locations and/or applications where sympathetic nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, cardiac ablation, pulmonary vein isolation, pulmonary vein ablation, tumor ablation, benign prostatic hyperplasia therapy, pain management, nerve excitation or blocking or ablation, modulation of muscle activity, hyperthermia or other warming of tissues, etc. The disclosed methods and apparatus can be applied to any relevant medical procedure, involving both human and non-human subjects. The term modulation refers to ablation and other techniques that may alter the function of affected nerves and other tissue.

FIG. 1 is a schematic view of an example sympathetic nerve ablation system 100. System 100 may include a sympathetic nerve ablation device 120. Sympathetic nerve ablation device 120 may be used to ablate nerves (e.g., renal nerves) disposed adjacent to the kidney K (e.g., renal nerves disposed about a renal artery RA). In use, sympathetic nerve ablation device 120 may be advanced through a blood vessel such as the aorta A to a position within the renal artery RA. This may include advancing sympathetic nerve ablation device 120 through a guide sheath or catheter 14. When positioned as desired, sympathetic nerve ablation device 120 may be activated to activate one or more electrodes (not shown). This may include operatively coupling sympathetic nerve ablation device 120 to a control unit 110, which may include an RF generator, so as to supply the desired activation energy to the electrodes. For example, sympathetic nerve ablation device 120 may include a wire or conductive member 18 with a connector 20 that can be connected to a connector 22 on the control unit 110 and/or a wire 24 coupled to the control unit 110. In at least some embodiments, the control unit 110 may also be utilized to supply/ receive the appropriate electrical energy and/or signal to activate one or more sensors disposed at or near a distal end of sympathetic nerve ablation device 120. When suitably activated, the electrodes may be capable of ablating tissue (e.g., sympathetic nerves) as described below and the sensors may be used to detect desired physical and/or biological parameters.

Figure 2:
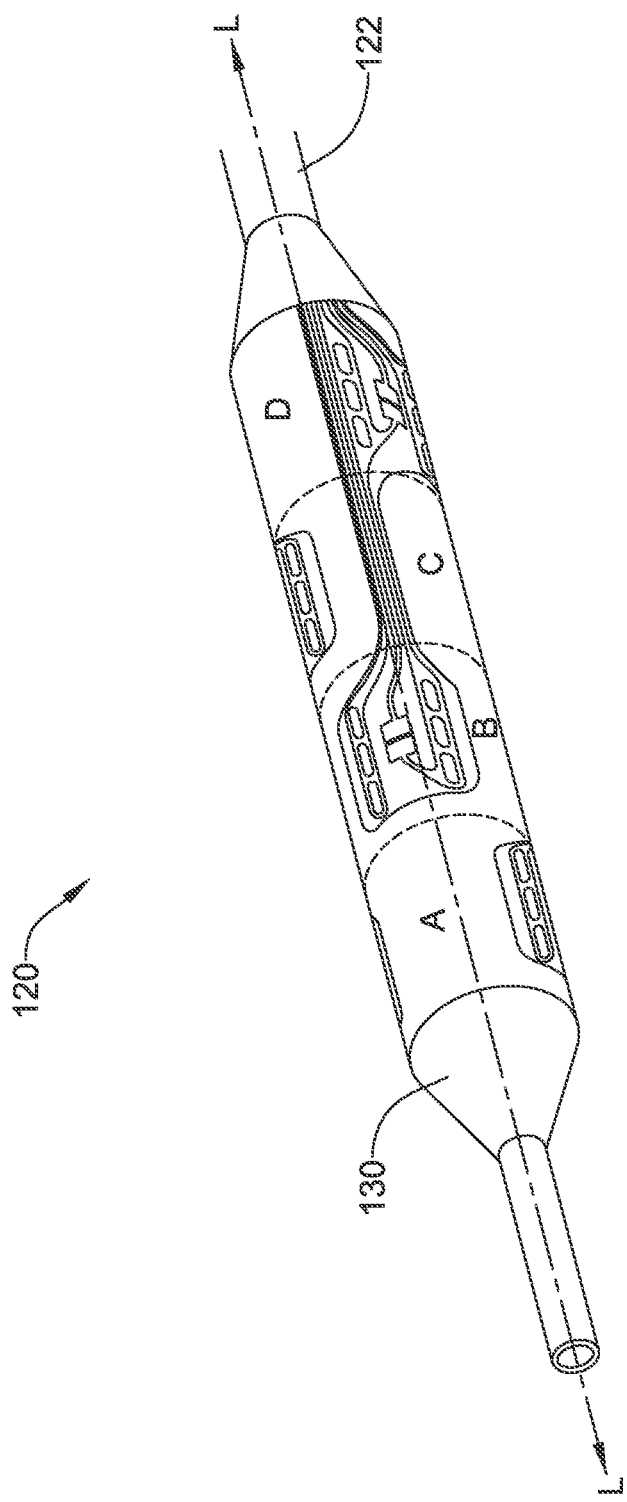
FIG. 2 is a perspective view of an example expandable member of a sympathetic nerve ablation device.

In some embodiments, the sympathetic nerve ablation device 120 may include an elongate tubular member or catheter shaft 122, as shown in FIG. 2. In some embodiments, the elongate tubular member or catheter shaft 122 may be configured to be slidingly advanced over a guidewire or other elongate medical device to a target site. In some embodiments, the elongate tubular member or catheter shaft 122 may be configured to be slidingly advanced within a guide sheath or catheter 14 to a target site. In some embodiments, the elongate tubular member or catheter shaft 122 may be configured to be advanced to a target site over a guidewire, within a guide sheath or catheter 14, or a combination thereof. An expandable member 130 may be disposed at, on, about, or near a distal region of the elongate tubular member or catheter shaft 122.

For example, as shown in FIG. 2, in some embodiments, the electrode assemblies may be arranged on the expandable member 130, shown here in an expanded state, according to a plurality of generally cylindrical treatment zones A-D. In other embodiments, the expandable member 130 or other components of the treatment system may include additional electrode assemblies that are not in a treatment zone or are otherwise not used or configured to deliver a treatment energy.

Figure 3:
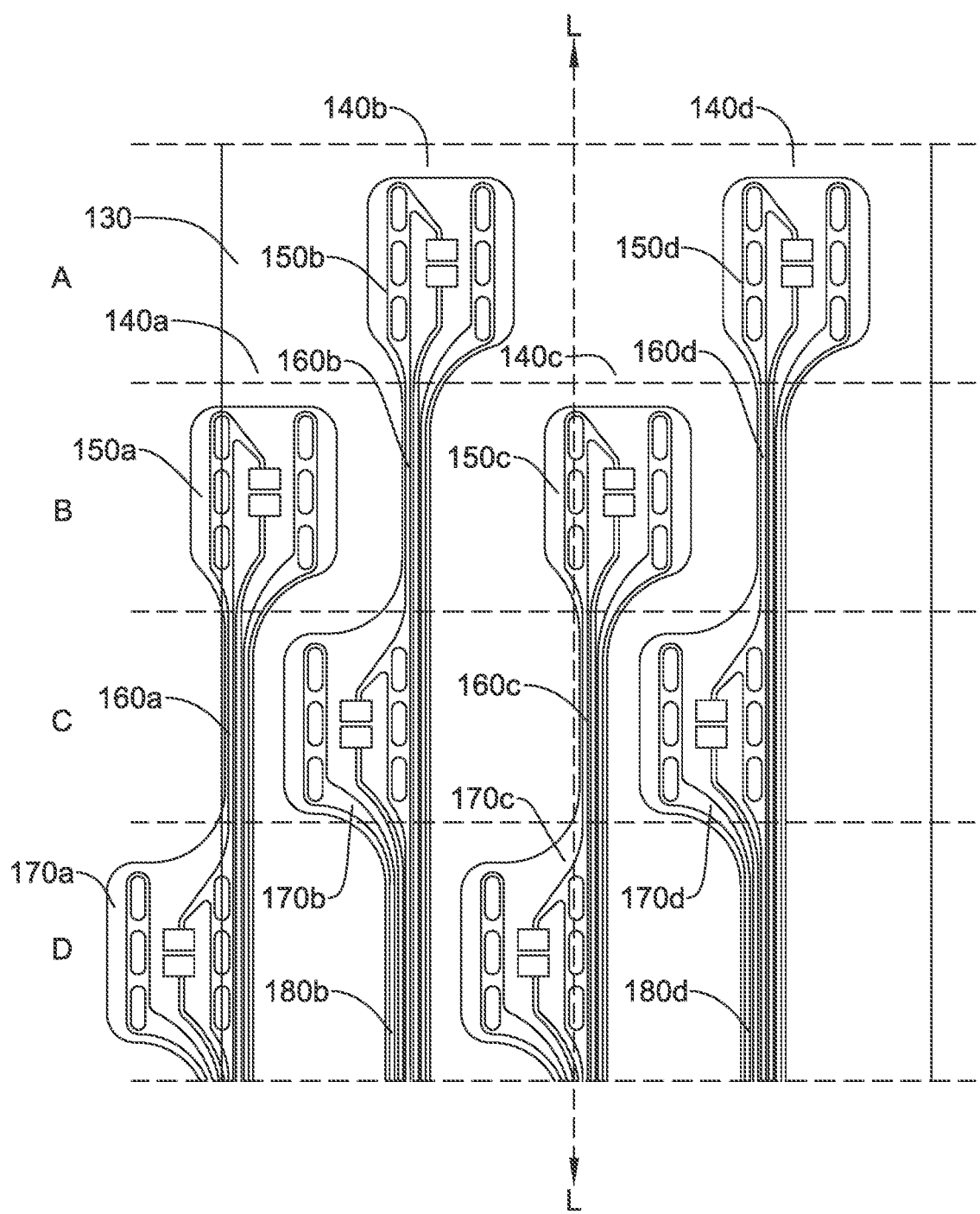
FIG. 3 is a partial top view of the expandable member of FIG. 2 in an unrolled or flat configuration.

The treatment zones A-D and associated electrode assemblies 140a-d are further illustrated in FIG. 3, which is an "unrolled" depiction of a portion of the expandable member 130 of FIG. 2. The treatment zones A-D may be longitudinally adjacent to one another along longitudinal axis L-L, and may be configured such that energy applied by the electrode assemblies create treatments that may or may not overlap. Treatments applied by the longitudinally adjacent bipolar electrode assemblies 140a-d may be circumferentially non-continuous along longitudinal axis L-L. For example, with reference to FIG. 3, lesions created in treatment zone A may in some embodiments minimize overlap about a circumference (laterally with respect to L-L in this view) with lesions created in treatment zone B. In other embodiments, however, the energy applied by the electrode assemblies, such as the electrode assemblies shown in FIG. 3, may overlap, longitudinally, circumferentially, and/or in other ways, to at least some extent. Each electrode pad assembly may include four elements, which are a distal electrode pad 150a-d, intermediate tail 160a-d, proximal electrode pad 170a-d, and proximal tail 180b,d (not shown for electrode pad assemblies 140b and 140c).

Figure 4A:
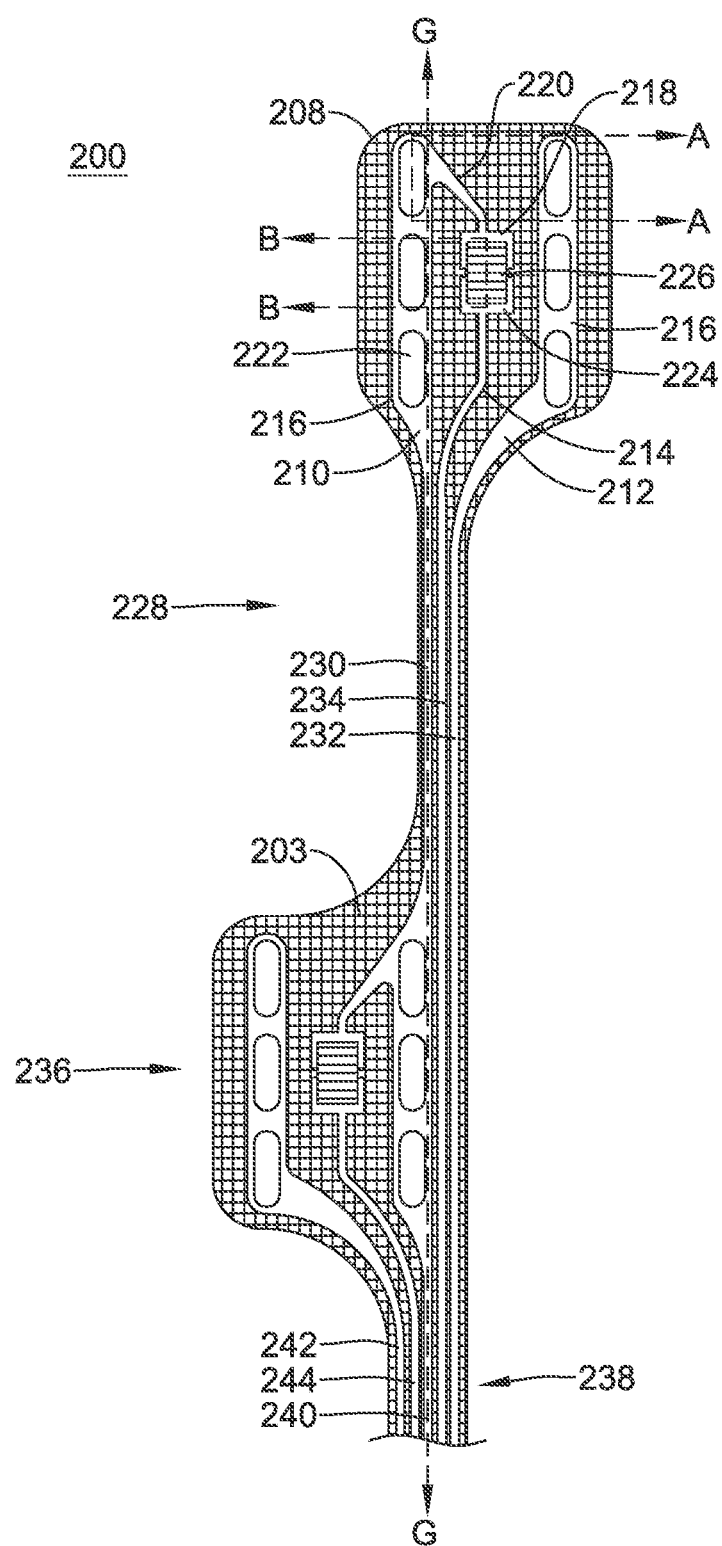
FIG. 4A is a top view of a portion of an example electrode assembly.

FIG. 4A shows a top view of an example electrode assembly 200. The electrode assembly 200 may be constructed as a flexible circuit having a plurality of layers. Such layers may be continuous or non-contiguous, i.e., made up of discrete portions. Shown in FIGS. 5 and 6, a base layer 202 of insulation may provide a foundation for the electrode assembly 200. The base layer 202 may be constructed from a polymer such as polyimide, although other materials are contemplated. A conductive layer 204 made up of a plurality of discrete traces may be layered on top of the base layer 202. The conductive layer 204 may be, for example, a layer of electrodeposited copper. Other materials are also contemplated. An insulating layer 206 may be discretely or continuously layered on top of the conductive layer 204, such that the conductive layer 204 may be fluidly sealed between the base layer 202 and the insulating layer 206. Like the base layer 202, the insulating layer 206 may be constructed from a polymer such as polyimide, although other materials are contemplated. In some embodiments, the insulating layer 206 may be from about 0.01 mm thick to about 0.02 mm thick. In other embodiments, the insulating layer 206 may be a complete or partial polymer coating, such as PTFE or silicone. Other materials are also contemplated.

The electrode assembly 200 shown in FIG. 4A may include a distal electrode pad 208. In this region, the base layer 202 may form a rectangular shape. This is not intended to be limiting. Other shapes are contemplated. The pads and other portions of the assemblies may include rounded or curved corners, transitions and other portions. The distal electrode pad 208 may include a plurality of discrete traces layered on top of the base layer 202. These traces may include a ground trace 210, an active electrode trace 212, and a sensor trace 214. The ground trace 210 may include an elongated electrode support 216 laterally offset from a sensor ground pad 218. The sensor ground pad 218 may be electrically coupled to the elongated electrode support 216 of the ground trace 210 and may be centrally located on the distal electrode pad 208. A bridge 220 may connect a distal most portion of the sensor ground pad 218 to a distal portion of the elongated electrode support 216 of the ground trace 210. The bridge 220 may taper down in width as it travels to the sensor ground pad 218. In some embodiments, the bridge 220 may have a relatively uniform and thin width to enable a desired amount of flexibility. The elongated electrode support 216 may taper down in width at its proximal end, however, this is not required. In some embodiments, the elongated electrode support 216 may abruptly transition to a much thinner trace at its proximal portion, to enable a desired amount of flexibility. Generally, the curvature of the traces where necking is shown may be optimized to reduce balloon recapture forces and the potential for any snagging that sharper contours may present. The shape and position of the traces may also be optimized to provide dimensional stability to the electrode assembly 200 as a whole, so as to prevent distortion during deployment and use.

The system 100 may be used to perform a method of treatment in accordance with one non-limiting embodiment of the disclosure. For example, the control unit 110 may be operationally coupled to the ablation device 120, which may be inserted into a body passageway such that an expandable member 130 (having a plurality of electrode assemblies) may be placed adjacent to a first section of the body passageway where therapy is required. Placement of the ablation device 120 at the first section of the body passageway where therapy is required may be performed according to conventional methods, e.g., over a guidewire under fluoroscopic guidance. Once inserted, the expandable member 130 may be made to expand from a collapsed delivery configuration to an expanded configuration, for example by pressurizing fluid from about 2-10 atm in the case of a balloon. This may cause the electrodes and/or electrode assemblies of the expandable member 130 to come into contact with the first section of the body passageway.

In some embodiments, the balloon may be made of polyethylene terephthalate (PET), and the base layer 202 may be bonded to the balloon with adhesive. The base layer 202 may be generally flat and stiffer than the softer round balloon. The generally flat electrode assembly 200 may resist conforming to the rounded balloon shape during refolding after use, which may require high withdrawal forces. In some cases, the generally flat electrode assembly 200 may create catch points at its edges which may lead to delamination of the electrode assembly 200.

The use of medical devices that include a balloon with a flex circuit coupled thereto, for example as described herein, may be desirable. In some instances, however, the flex circuits may include relatively stiff materials. Accordingly, if the balloon is deflated, the flex circuit may tend to flatten and/or widen out. When so configured, the flex circuit, or edges thereof, could catch on the edge of a guide catheter when proximally retracting the medical device (e.g., including the affixed flex circuits) into the guide catheter. Disclosed herein are medical devices that include structural features that may reduce the likelihood of a flex circuit or other structures of the medical device "catching" on the end of a guide catheter (or other device) when being retracted, for example, into the guide catheter, thus resulting in reduced withdrawal forces.

The base layer 202 may include a plurality of grooves, cuts, or indentations 203 to provide for added flexibility. In some embodiments, the grooves 203 and rounded or curved electrode pad edges may enhance the assembly's resistance to delamination from its expandable device, as may occur, in some instances, when the expandable device is repeatedly expanded and collapsed (which may also entail deployment from and withdrawal into a protective sheath), such as may be needed when multiple sites are treated during a procedure. The grooves 203 may result in a mechanically softened base layer 202, resulting in more controlled balloon refolding behavior and more robust balloon withdrawal with lower force required for withdrawal. In some embodiments, the grooves 203 may be placed in an orientation and number where refolding is desired. In some embodiments, such as that shown in FIG. 4E, the grooves 203 may be arranged at the corners of the electrode pads 208 to predispose the electrode assembly 200 to curling at the edge of the electrode pad 208 rather than remaining flat.

Figure 4E:
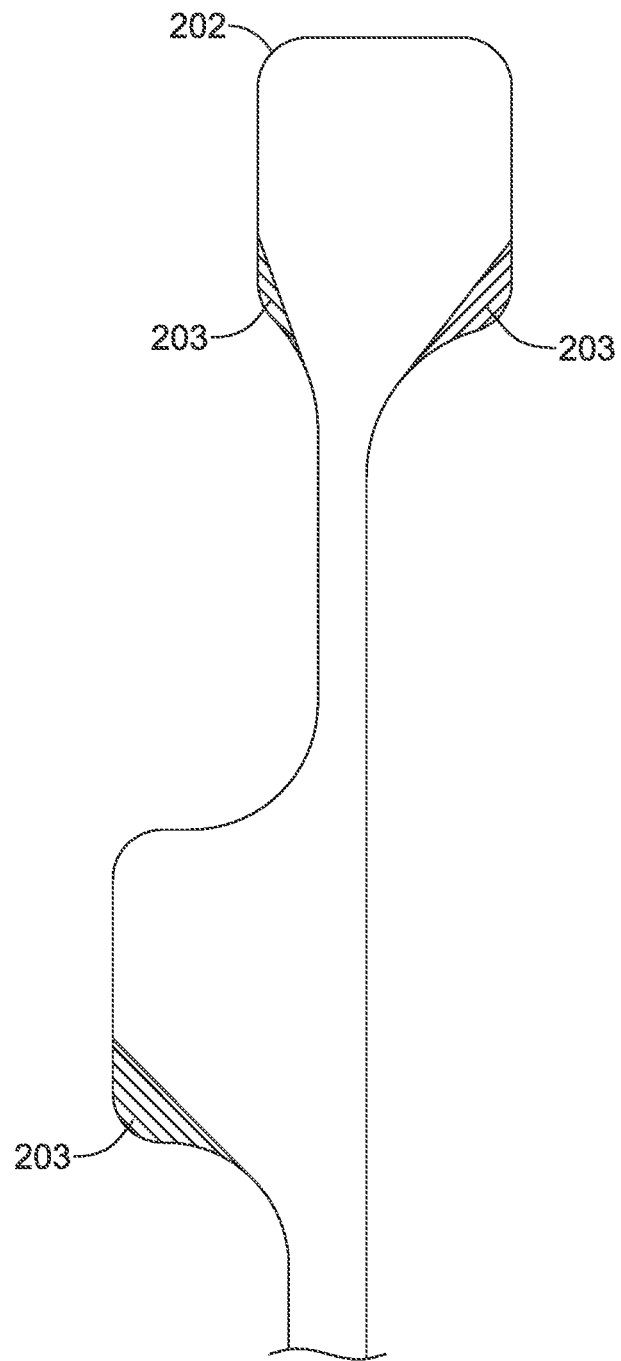
Figure 5:
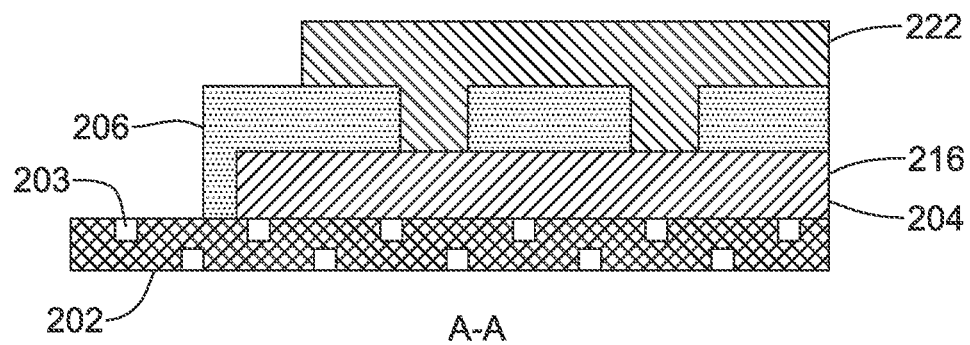
FIG. 5 is a partial cross-sectional view A-A of FIG. 4A.
Figure 6:
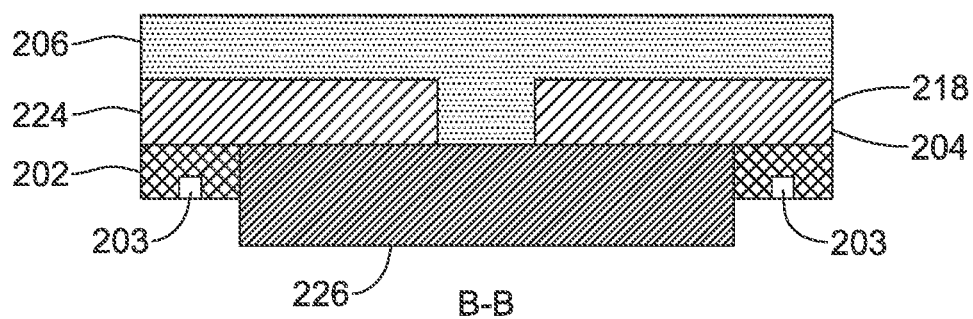
FIG. 6 is a partial cross-sectional view B-B of FIG. 4A.
Figure 7:
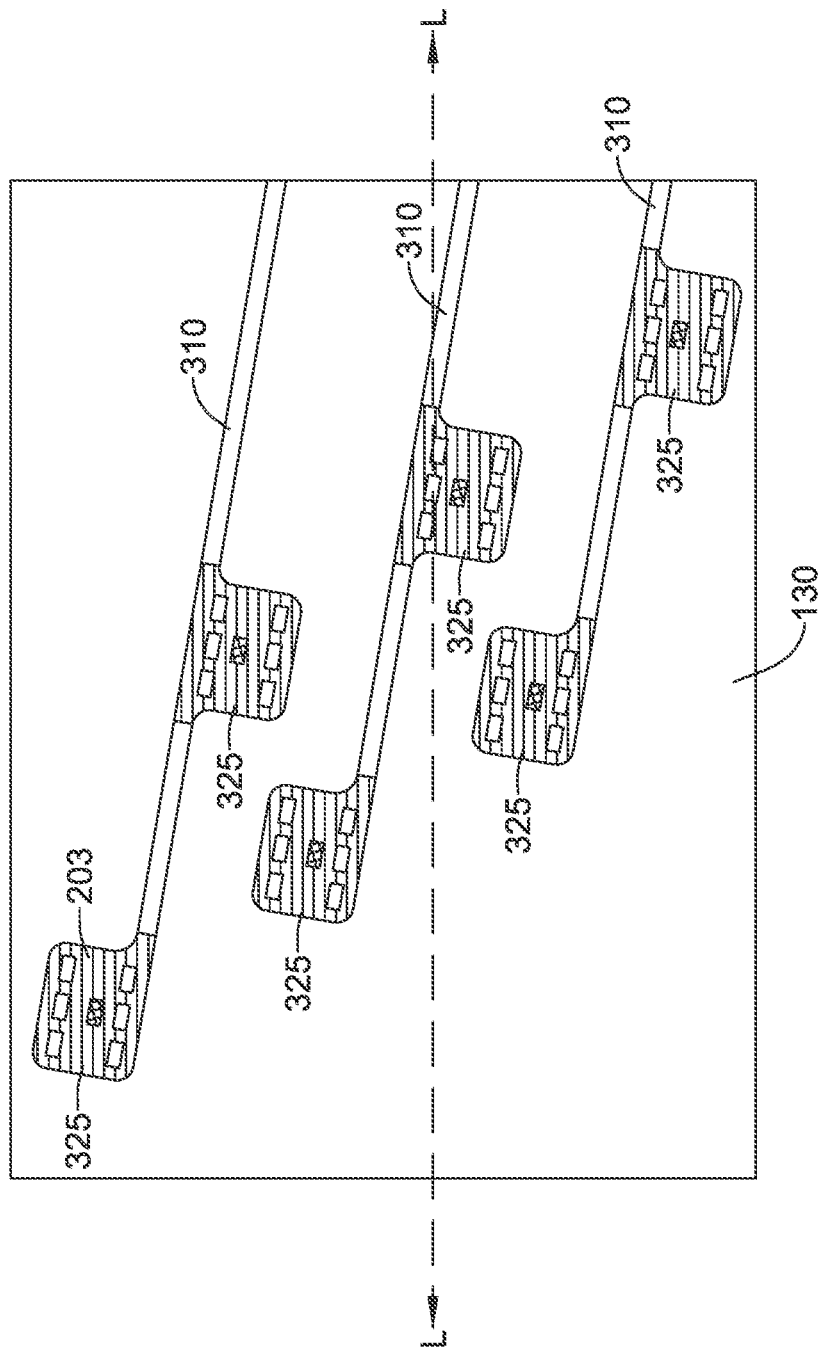
FIG. 7 is a partial top view of an alternative expandable member in an unrolled or flat configuration.

In some embodiments, the grooves 203 may be laser ablated or etched regions in the base layer 202. In at least some embodiments, the grooves 203 may be formed using an excimer laser. Alternatively, other lasers, other cutting tools including mechanical tools, or the like may be utilized. The grooves 203 may be regions where 5-80% of the total thickness of the base layer 202 is removed, or where about 5-60% of the total thickness of the base layer 202 is removed, or where about 10-40% of the total thickness of the base layer 202 is removed, or where about 10-20% of the total thickness of the base layer 202 is removed. These are just examples. The grooves 203 may be score lines, regions of compression, or cuts in the base layer 202. The grooves 203 may be formed using a process that results in a region of reduced thickness of the base layer 202 or otherwise results in a region of the base layer 202 that folds, buckles, or bends along the line of grooves 203. The grooves 203 may be made in only a top or bottom surface of the base layer 202, or may be made in both the top and bottom surface of the base layer 202. In embodiments with grooves 203 in both the top and bottom surface, the grooves 203 in the top surface may be aligned with the grooves 203 in the bottom surface. In other embodiments, grooves 203 in the top surface may be offset from grooves 203 in the bottom surface of base layer 202, as shown in FIG. 5. In some embodiments, grooves 203 may be made over the entire surface of the base layer 202, as shown in FIG. 4A. In some embodiments, grooves 203 may be made over a portion of the base layer 202, as shown in FIG. 4E. In some embodiments, the grooves 203 may be made in the base layer 202 in the region of the electrode pad 208, as shown in FIG. 7.

The grooves 203 may be made in the base layer 202 before the conductive layer 204 or other layers are added. In some embodiments, the ablation device 120 may be made by forming the grooves 203 in the base layer 202, forming an electrical circuit on the grooved base layer 202 to create an electrode assembly 200, affixing the grooved electrode assembly 200 onto an expandable member 130, and attaching the expandable member 130 to a catheter shaft (e.g., catheter shaft 122).

Figure 4B:
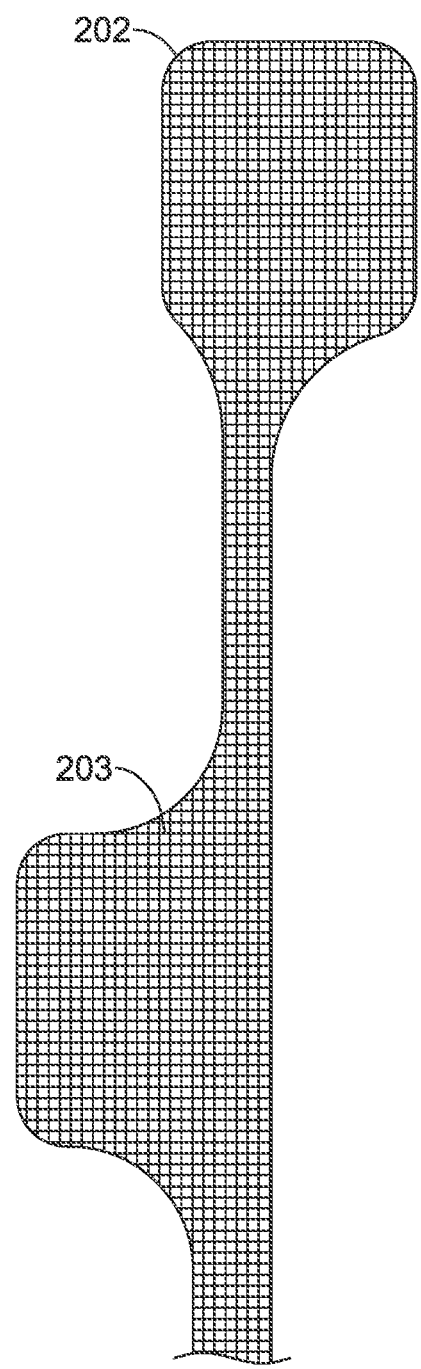
FIGS. 4B-4H are top or bottom views of a portion of example base layers showing various different groove configurations.
Figure 4C:
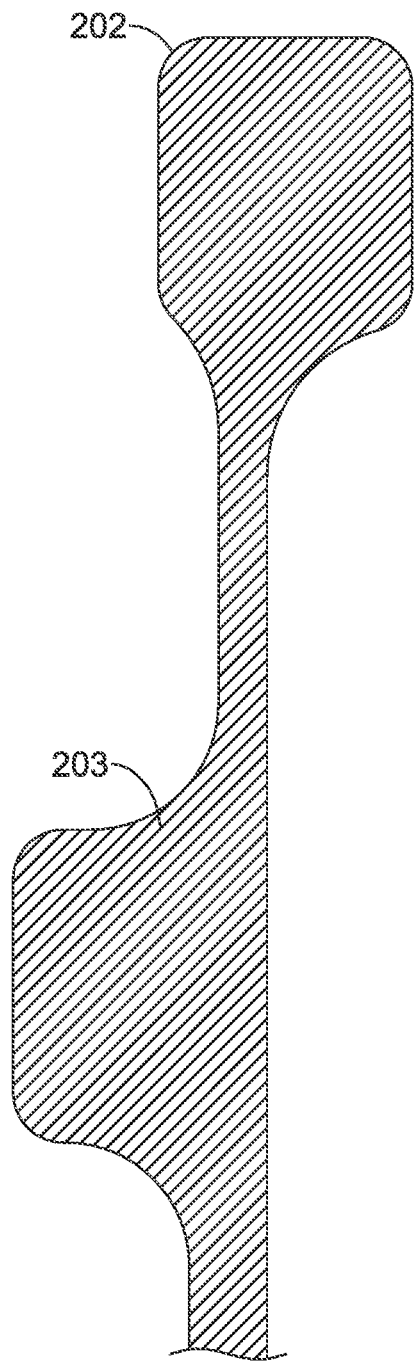
Figure 4D:
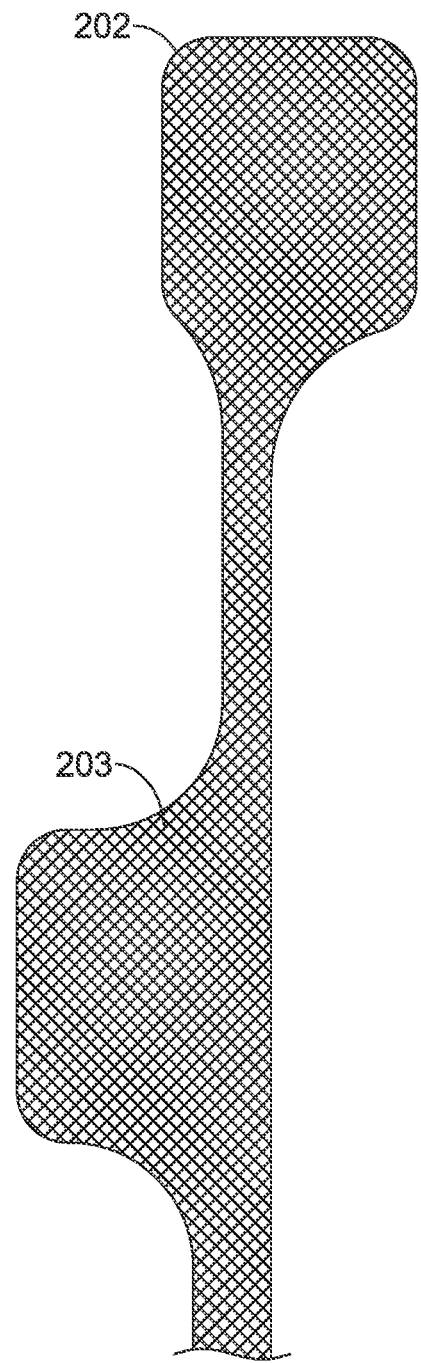
Figure 4F:
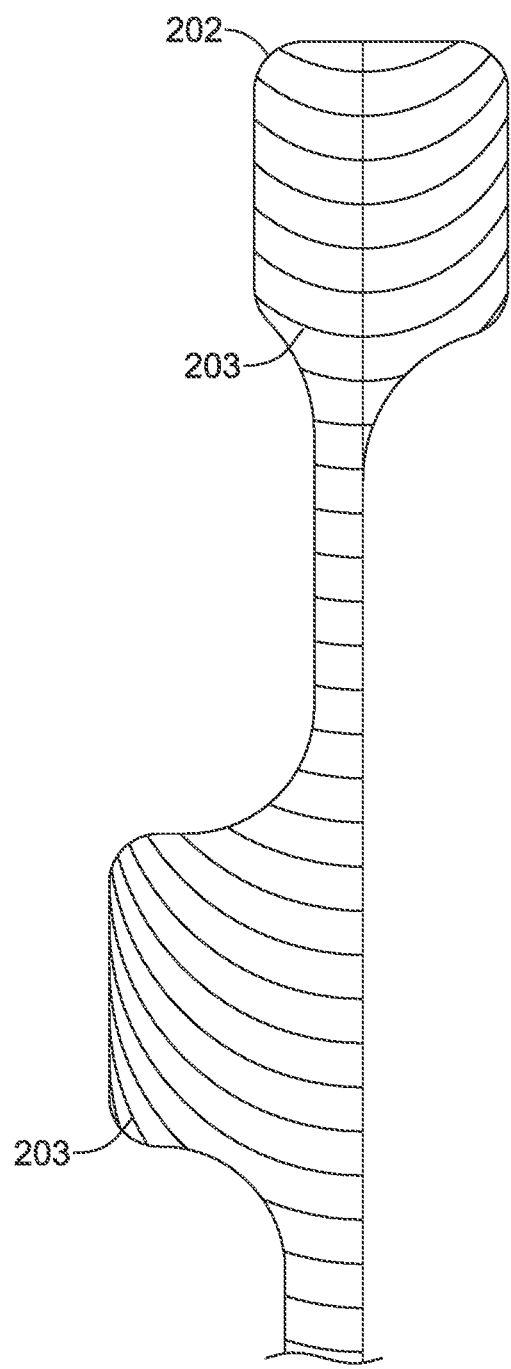
Figure 4G:
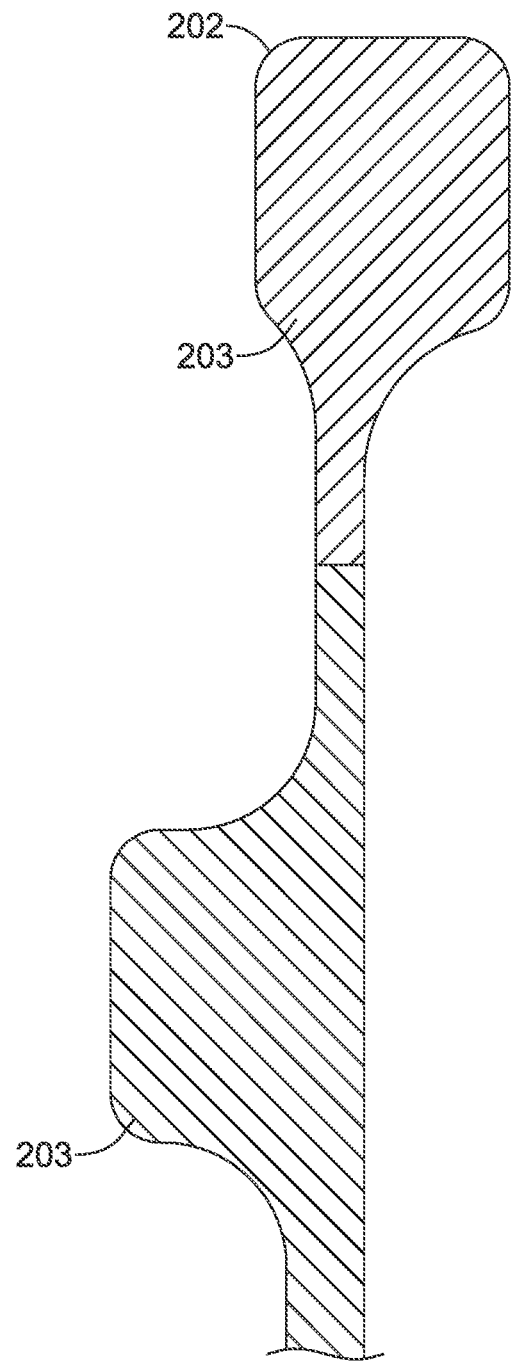
Figure 4H:
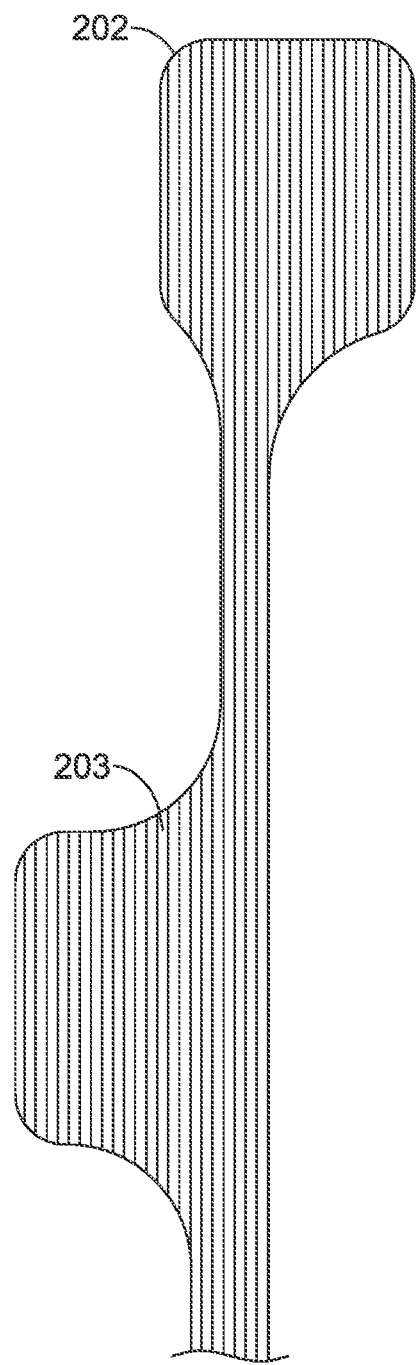

In some embodiments, the grooves 203 may form a grid or crosshatching, such as shown in FIGS. 4A, 4B, and 4D. In some embodiments, the grooves 203 may be a series of generally parallel lines, as shown in FIGS. 4C and 4H. The grooves 203 may be oriented in any direction relative to a central axis G-G of the electrode assembly 200. In some embodiments, the grooves are generally parallel to the central axis G-G of the electrode assembly 200, as shown in FIG. 4H. Longitudinal grooves may provide radial flexibility to the electrode assembly 200. In some embodiments, the grooves 203 include grooves both parallel and perpendicular to the central axis G-G, as shown in FIGS. 4A and 4B. In some embodiments, the grooves are oriented at an angle to the central axis, as shown in FIGS. 4C and 4D. In some embodiments, the grooves 203 may be located only at the corners of the electrode pad 208, as shown in FIG. 4E. In some embodiments, the grooves 203 are curved, as shown in FIG. 4F. In some embodiments, the base layer 202 may include a plurality of different regions having grooves 203 in different orientations, as shown in FIGS. 4E, 4F and 4G.

FIG. 5 shows a partial cross-section A-A of the distal electrode pad 208. An electrode 222 is shown layered over a portion of the insulating layer 206, which may have a plurality of passages (e.g., holes) to enable the electrode 222 to couple to the elongated electrode support 216 of the ground trace 210 of conductive layer 204. FIG. 5 shows grooves 203 in the top surface offset from grooves 203 in the bottom surface of the base layer 202.

As shown in FIG. 4A, the ground electrode trace 210 and active electrode trace 212 may include a plurality of electrodes. Three electrodes 222 may be provided for each electrode trace, however, more or less may be used. Additionally, each electrode 222 may have radiused corners to reduce tendency to snag on other devices and/or tissue. Although the above description of the electrodes 222 and the traces associated with them has been described in the context of a bi-polar electrode assembly, those of skill in the art will recognize that the same electrode assembly may function in a monopolar mode as well. For instance, as one non-limiting example, the electrodes associated with active electrode traces 212 and 242 may be used as monopolar electrodes, with ground trace 210 disconnected during energization of those electrodes.

The sensor trace 214 may be centrally located on the distal electrode pad 208 and may include a sensor power pad 224 facing the sensor ground pad 218. These pads may connect to power and ground poles of a temperature sensor 226, such as a thermocouple (for example, Type T configuration: Copper/Constantan) or thermistor, as shown in the partial cross-section depicted in FIG. 6.

The temperature sensor 226 may be proximately connected to the sensor power pad 224 and may be distally connected to the sensor ground pad 218. To help reduce overall thickness, the temperature sensor 226 may be positioned within an opening within the base layer 202. In some embodiments, the temperature sensor 226 may be a thermistor. As shown, the temperature sensor 226 may be on a non-tissue contacting side of the distal electrode pad 208.

Accordingly, the temperature sensor 226 may be captured between the electrode structure and a balloon when incorporated into a final device, such as ablation device 120. This may be advantageous since surface-mounted electrical components, like thermistors, typically have sharp edges and corners, which may get caught on tissue and possibly cause problems in balloon deployment and/or retraction. This arrangement may also keep soldered connections from making contact with blood, since solder is typically non-biocompatible. Further, due to the placement of the temperature sensor, it may measure temperature representative of tissue and the electrodes 222.

From the distal electrode pad 208, the combined base layer 202, conductive layer 204, and insulating layer 206 may reduce in lateral width to an intermediate tail 228. As shown in FIG. 4A, here, the conductive layer 204 may be formed to include an intermediate ground line 230, intermediate active electrode line 232, and intermediate sensor line 234, which may be respectively coextensive traces of the ground trace 210, active electrode trace 212, and sensor trace 214 of the distal electrode pad 208.

From the intermediate tail 228, the combined base layer 202, conductive layer 204, and insulating layer 206 may increase in lateral width to form a proximal electrode pad 236. The proximal electrode pad 236 may be constructed similarly to the distal electrode pad 208, with the electrode geometry and temperature sensor arrangement being essentially identical, although various differences may be present. However, as shown, the proximal electrode pad 236 may be laterally offset from the distal electrode pad 208 with respect to the central axis G-G extending along the intermediate ground line 230. The intermediate active electrode line 232 and intermediate sensor line 234 may be laterally coextensive with the proximal electrode pad 236 on parallel respective axes with respect to central axis G-G.

From the proximal electrode pad 236, the combined base layer 202, conductive layer 204, and insulating layer 206 may reduce in lateral width to form a proximal tail 238. The proximal tail 238 may include a proximal ground line 240, proximal active electrode line 242, and proximal sensor line 244, as well the intermediate active electrode line 232 and intermediate sensor line 234. The proximal tail 238 may include connectors (not shown) to enable coupling to one or more sub-wiring harnesses and/or connectors and ultimately to control unit 110. Each of these lines may be extended along parallel respective axes with respect to central axis G-G.

As shown, the electrode assembly 200 may have an asymmetric arrangement of the distal electrode pad 208 and proximal electrode pad 236, about axis G-G. Further, the ground electrodes of both electrode pads may be substantially aligned along axis G-G, along with the intermediate and proximal ground lines 230/240. It has been found that this arrangement may present certain advantages. For example, by essentially sharing the same ground trace, the width of the proximal tail may be only about one and a half times that of the intermediate tail 228, rather than being approximately twice as wide if each electrode pad had independent ground lines. Thus, the proximal tail 238 may be narrower than two of the intermediate tails 228.

In some embodiments, a plurality of electrode assemblies 310 may be twisted or canted at an angle from the longitudinal axis L-L of the expandable member 130, as shown in FIG. 7. The angled electrode assemblies 310 may be disposed along or otherwise define pre-determined fold lines along which the expandable member 130 may fold after deflation. In some embodiments, angled electrode assemblies 310 may aid in twisting and re-folding of the expandable member 130. In some embodiments, the grooves 203 may be substantially parallel to the longitudinal axis L-L of the expandable member 130, as shown in FIG. 7. In other embodiments, the grooves 203 may include cross-hatching, may extend at an angle to the longitudinal axis L-L, may extend over only a portion of the electrode assembly 310, may be curved, or may extend at different angles in different regions, similar to the grooves shown in FIGS. 4B-4H.

The electrode assemblies 310 may be substantially linear along their length, extending at an angle from the longitudinal axis along the entire length of the expandable member 130. In other embodiments, the electrode assemblies may extend parallel to the longitudinal axis in a proximal region, and then be bent into an angled orientation in a distal region (not shown). The angled electrode assemblies 310 may cause the balloon to rotate and fold along the lines of the angled elongate members 310, reducing the withdrawal force needed to withdraw the ablation device 300 into a guide sheath or catheter 14, and allowing the use of a smaller diameter guide sheath. For example, a 6 Fr or 7 Fr guide catheter 14 may be used, providing advantages in renal procedures, rather than 8 Fr guide catheters which have been previously used. The angled electrode assemblies 310 may reduce shear force or improve balloon refold profile efficiency, thereby reducing delamination of the electrode assemblies from the expandable member 130. In some embodiments, the base layer 202 of the angled electrode assemblies 310 may have grooves 203 oriented as discussed above with regard to FIGS. 4A-4G. In some embodiments, as shown in FIG. 7, the grooves 203 may extend over only the region of the electrode pads 325, and the grooves 203 may extend in different directions relative to the longitudinal axis L-L.

The electrode assemblies 310 may be similar in form and function to the electrode assemblies and/or flex circuits disclosed herein (e.g., electrode assembly 200). In at least some embodiments, the electrode assemblies 310 may be attached directly to the expandable member 130, and each electrode assembly 310 may contain one or more electrode pads 325. Each electrode pad 325 may include one or more ground electrodes, one or more active electrodes, and a temperature sensor as discussed above. In some embodiments, the electrodes and sensors of each electrode pad 325 may be arranged as shown in FIG. 4A. The electrode pads 325 on adjacent electrode assemblies 310 may be offset, as shown in FIG. 7. In other embodiments, the electrode pads 325 may have a helical orientation along the length of the expandable member 130 that forms at least one complete (360 degree) circumferential loop within the lumen or vessel that the expandable member 130 is positioned. The electrode pads 325 may provide heating at a location within the tissue surrounding the body passageway without damaging the wall of the body passageway in order to disrupt the nerves located in the tissue surrounding the body passageway wall. A helical orientation is desirable to help avoid an increased risk of stenosis that may be present when electrodes are disposed within a single plane normal to a longitudinal axis of the body passageway (i.e., a circular electrode or group of electrodes forming a circumferential ring).

Figure 8:
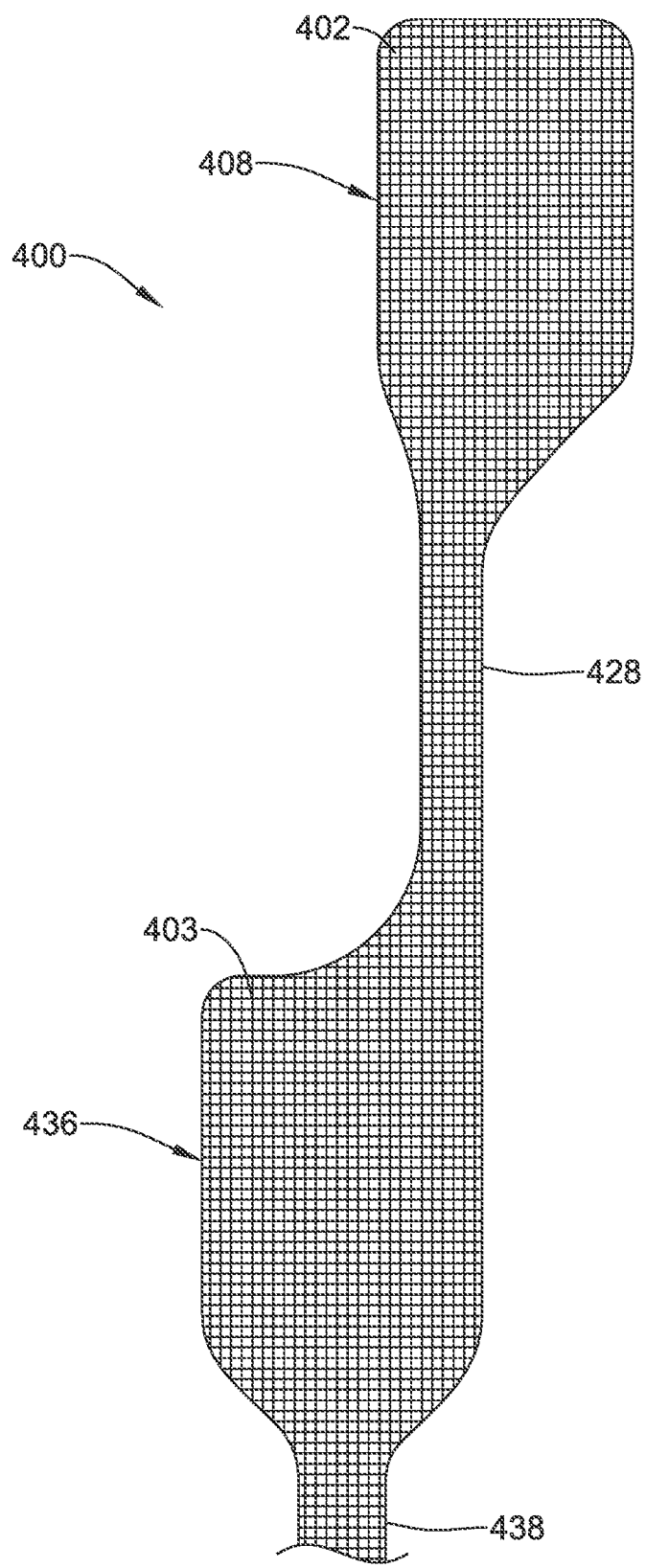
FIG. 8 is a top or bottom view of a portion of another example electrode assembly.

In at least some embodiments, the form or arrangement of the electrode assemblies vary include further variations. For example, FIG. 8 illustrates another example electrode assembly 400 that may be similar in form and function to other electrode assemblies disclosed herein. The electrode assembly 400 may include a distal electrode pad 408 and a proximal electrode pad 436. The electrode pads 408/436 may include electrodes, traces, temperature sensors, and the like similar to the electrode assembly 200 as shown in FIG. 4A. In addition, in at least some embodiments, the electrode assembly 400 may be coupled to a balloon and/or expandable member (e.g., expandable member 130). The electrode assembly 400 may include a base layer 402 having one or more grooves 403 formed therein. The base layer 402 may be disposed along a top and/or bottom surface of the electrode assembly 400 such that the grooves 403 may be disposed along the top surface, the bottom surface, or both. The grooves 403 may be arranged in a suitable pattern including any of those patterns disclosed herein.

An intermediate tail 228 may extend between the pads 408/436. A proximal tail 438 may extend proximally from the proximal electrode pad 436. In this example, the proximal electrode pad 436 may be centered with the proximal tail 438. In other words, the proximal tail 438 may be positioned so that it joins with the middle of the proximal electrode pad 436. Accordingly, the proximal electrode pad 436 may extend laterally relative to or otherwise from the proximal tail 438 in an essentially symmetrical manner (e.g., extending laterally the same distance from the proximal tail 438 on both sides). It can also be seen that the angle formed by the proximal electrode pad 436 and the proximal tail 438 where the proximal electrode pad 436 extends laterally is substantially the same on both sides of the proximal electrode pad 436. This arrangement may be desirable for a number of reasons. For example, by centering the proximal electrode pad 436 with the proximal tail 438, it may be less likely for the proximal electrode pad 436 to snag or catch on the end of a catheter or sleeve if the electrode assembly 400 is retracted therein.

It should also be understood that in other embodiments, the intermediate tail 228, which may also be centered on the pads 408/436. For example, intermediate tail 228 may extend between the pads 408/436, and may be centered on the proximal electrode pad 436, a distal electrode pad 408, or both pads 408/436.

In other words, the intermediate tail 228 may be positioned so that it joins with the middle of the proximal electrode pad 436, the middle of the distal electrode pad 408, or the middle of both pads 408/436. Accordingly, the proximal electrode pad 436, the distal electrode pad 408, or both, may extend laterally relative to or otherwise from the intermediate tail 228 in an essentially symmetrical manner (e.g., extending laterally the same distance from the intermediate tail 228 on both sides). In some cases, the angle formed by the proximal electrode pad 436 and the intermediate tail 228 where the proximal electrode pad 436 extends laterally is substantially the same on both sides of the proximal electrode pad 436. Similarly, in some cases, the angle formed by the distal electrode pad 408 and the intermediate tail 228 where the distal electrode pad 408 extends laterally is substantially the same on both sides of the distal electrode pad 408. This arrangement may be desirable for a number of reasons. For example, by centering the proximal electrode pad 436 and/or distal electrode pad 408 with the intermediate tail 228, it may be less likely for the electrode pad 436 to snag or catch on the end of a catheter or sleeve if the electrode assembly 400 is advanced and/or retracted therein.

In use, the ablation device 120 may be advanced through a blood vessel to a position adjacent to a target tissue (e.g., within a renal artery). In some embodiments, the target tissue may be one or more renal nerves disposed about the renal artery. When suitably positioned, expandable member 130 may be expanded from a collapsed delivery configuration to an expanded configuration. This may place the active electrodes against the wall of the blood vessel. The active electrodes may be activated. Ablation energy may be transmitted through the active electrodes through the target tissue (where renal nerves may be ablated, modulated, or otherwise impacted), and back through the ground electrodes, in a bipolar configuration, or back through the common ground electrode, in a monopolar configuration.

The materials that can be used for the various components of the ablation device 120 (and/or other devices disclosed herein) may include those commonly associated with medical devices. For simplicity purposes, the following discussion makes reference to the ablation device 120. However, this is not intended to limit the devices and methods described herein, as the discussion may be applied to other similar tubular members and/or expandable members and/or components of tubular members and/or expandable members disclosed herein.

The ablation device 120 and the various components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL®

400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions of the ablation device 120 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the ablation device 120 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the ablation device 300 to achieve the same result.

In some embodiments, a degree of Magnetic Resonance Imaging (MRI) compatibility may be imparted into the ablation device 120. For example, portions of device, may be made of a material that does not substantially distort the image and create substantial artifacts (i.e., gaps in the image). Certain ferromagnetic materials, for example, may not be suitable because they may create artifacts in an MRI image. In some of these and in other embodiments, portions of the ablation device 300 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

U.S. patent application Ser. No. 13/750,879, filed on Jan. 25, 2013, entitled "METHODS AND APPARATUSES FOR REMODELING TISSUE OF OR ADJACENT TO A BODY PASSAGE", now U.S. Patent Publication US20130165926A1, is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method for treating a body lumen wall, the method comprising:

placing a distal end of a catheter proximate to the body lumen wall, the distal end including an expandable member having a longitudinal axis and a body extending along the longitudinal axis, a plurality of flexible elements on the body of the expandable member, each of the plurality of flexible elements including a substrate having a plurality of elongate grooves formed therein and at least one electrode assembly, wherein the at least one electrode assembly is disposed over the substrate and at least a portion of the plurality of elongate grooves;

expanding the expandable member to place one or more of the at least one electrode assembly in sufficient proximity to tissue of a portion of the body lumen wall, so as to allow energy to be transferred to the tissue; and energizing the at least one electrode assembly placed in proximity to the tissue, so as to apply energy sufficient to treat the tissue.

2. The method of claim 1, wherein at least a portion of the plurality of elongate grooves extend along the substrate at an angle from the longitudinal axis of the expandable member.

3. The method of claim 1, wherein the plurality of elongate grooves extends along the substrate in more than one direction.

4. The method of claim 1, wherein at least a portion of the plurality of elongate grooves are substantially parallel to each other.

5. The method of claim 1, wherein at least a portion of the plurality of elongate grooves defines a cross-hatched pattern.

6. The method of claim 1, wherein the plurality of elongate grooves extends over substantially an entire length of the substrate.

7. The method of claim 1, wherein the plurality of elongate grooves extends over only select regions of the substrate.

8. A method of treatment, the method comprising:
inserting a catheter into a body lumen, the catheter including an expandable member disposed along a distal end of the catheter, the expandable member having a body extending along a longitudinal axis and at least one flexible substrate attached to the expandable member, the substrate including a plurality of elongate grooves and one or more electrode assemblies;

electrically contacting at least one of the one or more of the electrode assemblies with tissue of the body lumen, and applying energy treatment to the tissue from the one or more electrode assemblies in contact with the body lumen; and controlling contraction of the expandable member along predisposed fold lines coincident with at least one of the plurality of elongate grooves after applying the energy treatment.

9. The method of claim 8, wherein the plurality of elongate grooves is disposed in a pre-determined pattern of the predisposed fold lines.

10. The method of claim 8, wherein the contacting step comprises flexing the at least one flexible substrate along the predisposed fold lines in the expandable member, the predisposed fold lines having an axis coincident with an axis of at least one of the plurality of elongate grooves.

11. The method of claim 8, wherein the plurality of elongate grooves extends over substantially an entire length of the at least one flexible substrate.

12. The method of claim 8, wherein the plurality of elongate grooves extends over only select regions of the at least one flexible substrate.

13. The method of claim 8, wherein the plurality of elongate grooves extends along the at least one flexible substrate in more than one direction.

14. The method of claim 8, wherein at least a portion of the plurality of elongate grooves are substantially parallel to each other.

15. A method for treating a body lumen wall, the method comprising:
placing a distal end of a catheter proximate to the body lumen wall, the distal end including an expandable member having a body extending along a longitudinal axis, a plurality of flexible elements on the body of the expandable member, each of the plurality of flexible elements including a substrate having areas of reduced thickness defining a plurality of grooves extending along the substrate and one or more electrode assemblies, the one or more electrode assemblies being disposed over the substrate and at least a portion of the plurality of grooves; and expanding the expandable member to place one or more of the plurality of flexible elements in proximity to tissue of a portion of the body lumen wall being treated, the substrate of the plurality of flexible elements having greater flexibility in the areas of reduced thickness compared to areas of the substrate without the plurality of grooves, the plurality of grooves flexing to conform the substrate to an outer contour of the body during expansion, such that the one or more electrode assemblies contact the tissue of the portion of the body lumen wall, and applying energy treatment to the tissue from the one or more electrode assemblies in contact with the body lumen wall.

16. The method of claim 15, wherein the one or more electrode assemblies on adjacent flexible elements of the plurality of flexible elements are longitudinally offset.

17. The method of claim 15, wherein the one or more electrode assemblies comprise a distal electrode pad, a distal tail extending proximally from the distal electrode pad, a proximal electrode pad, a proximal tail extending proximally from the proximal electrode pad, and a central axis; and wherein the proximal electrode pad is laterally offset from the distal electrode pad with respect to the central axis.

18. The method of claim 15, wherein the plurality of grooves is disposed in only one of an upper and a lower surface of the substrate.

19. The method of claim 15, wherein the plurality of grooves is disposed in both an upper and a lower surface of the substrate.

* * * * *